(12) United States Patent
Zhang et al.

(10) Patent No.: US 7,378,557 B1
(45) Date of Patent: May 27, 2008

(54) METHODS FOR PREPARING ISOLONGIFOLENONE AND ITS USE IN REPELLING ARTHROPODS

(75) Inventors: Aijun Zhang, Silver Spring, MD (US); John Carroll, Beltsville, MD (US); Shifa Wang, Nanjing (CN); Jerome A. Klun, Potomac, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/777,795

(22) Filed: Jul. 13, 2007

(51) Int. Cl.
*C07C 45/27* (2006.01)
*A61K 31/12* (2006.01)
*A01N 25/34* (2006.01)

(52) U.S. Cl. .................. 568/342; 568/346; 514/690; 424/403

(58) Field of Classification Search .................. None
See application file for complete search history.

(56) References Cited

U.S. PATENT DOCUMENTS 3,647,847 A * 3/1972 Curtis et al. ................ 560/249
5,030,739 A * 7/1991 Foricher et al. ............ 552/542
6,734,159 B2 * 5/2004 Pickenhagen et al. ........ 512/19

\* cited by examiner

*Primary Examiner*—Sikarl A. Witherspoon
(74) *Attorney, Agent, or Firm*—John D. Fado; G. Byron Stover

(57) ABSTRACT

A method for making isolongifolenone involving reaction (−)-isolongifolene with chromium hexacarbonyl and t-butyl hydroperoxide. Also the use of isolongifolenone to repel arthropods by treating an object or area with an arthropod repelling effective amount of isolongifolenone (and optionally a carrier or carrier material).

18 Claims, 4 Drawing Sheets

METHODS FOR PREPARING ISOLONGIFOLENONE AND ITS USE IN REPELLING ARTHROPODS

BACKGROUND OF THE INVENTION

The present invention relates to a method for making isolongifolenone involving reacting (−)-isolongifolene with chromium hexacarbonyl and t-butyl hydroperoxide. The present invention also relates to the use of isolongifolenone to repel arthropods by treating an object or area with an arthropod repelling effective amount of isolongifolenone (and optionally a carrier or carrier material).

Diseases transmitted by blood-feeding arthropods are a serious threat to public health worldwide. More than 700 million cases of mosquito transmitted disease were reported annually (Shell, E. R., Atlantic Monthly, pp. 45-60, August 1997). Over 3 million people live under the threat of malaria, which kills over a million people each year (WHO World Malaria Report 2005, Roll Back Malaria, World Health Organization, UNICEF, http://rbm.who.int/wmr2005). In the United States, West Nile virus was transmitted by mosquitoes to more than 8,000 people from 1999-2005, resulting in over 780 deaths (DeBiasi, R. L., and K. L. TYLER, Nat. Clin. Pract. Neurol., 2:264-275 (2006)). N,N-Diethyltoluamide (Deet) is considered to be the best insect repellent ever developed and is the most widely used insect repellent worldwide with tens of millions of dollars in annual sales (Osimitz, T. G., and R. H. Grothaus, J. Am. Mosq. Control. Assoc., 11: 274-278 (1995)). However, Deet is a plasticizer and clinical literature reports the association of Deet with neurotoxicity in humans (Robbins, P. J., and M. G. Cherniack. J. Toxicol. Environ. Health, 18: 503-525 (1986)). Thus, there is a great need for effective alternatives to Deet.

We have found that isolongifolenone, which occurs in nature in trace amounts, is more effective than Deet in repelling ticks and deterring feeding mosquitoes. With high repellent efficiency, this compound will allow much wider application by the public and the military. Therefore, isolongifolenone has a great potential to displace Deet in the worldwide repellent marker.

Heretofore, isolongifolenone was most often obtained in large quantities by isomerization of longifolene, an abundant bridged tricyclic sesquiterpene found in turpentine oil from commercially available oleoresin of the Himalayan pine, *Pinus longfolia* Boxb (Ranganathan, R., et al., Tetrahedron, 26: 621-630 (1970)), to isolongifolene (U.S. Pat. No. 6,734, 159) with subsequent oxidation by oxygen, air, or metal oxidants (Dauben, W. G., et al., J. Org. Chem., 34: 3587-3592 (1969); Lala, L. K., and J. B. Hall, J. Org. Chem., 35: 1172-1173 (1970); Mihelich, E. D., and D. J. Eickhoff, J. Org. Chem., 48: 4135-4137 (1983); Mequillin, F. J., and M. Wood, J. Chem. Res. Miniprint, 3: 0755-0757 (1997)). However, these oxidation methods involved long reaction times and gave poor yields and unwanted by-products that were difficult to separate from the desired compound, isolongifolenone, because of the great similarity of their physical and chemical properties to isolongifolenone (Prahlad, J. R., et al., Tetrahedron Lett. 5: 417-427 (1964); Shieh, B. J., et al., Nippon Kagaku Kaishi, 906-908 (1978); U.S. Pat. No. 5,030,739; U.S. Pat. No. 6,734,159).

We have developed a facile and efficient method for producing pure isolongifolenone in a short time and at high yield which will make it less expensive and allow wide availability of this chemical for various industrial and clinical usages and especially for programs aimed at controlling malaria, West Nile virus, Lyme disease, and other diseases by suppressing human blood-feeding by the arthropods that vector these diseases.

SUMMARY OF THE INVENTION

In accordance with the present invention there is provided a method for making isolongifolenone involving reacting (−)-isolongifolene with chromium hexacarbonyl and t-butyl hydroperoxide. Also in accordance with the present invention there is provided a method for its use in repelling arthropods involving treating an object or area with an arthropod repelling effective amount of isolongifolenone (and optionally a carrier or carrier material).

DETAILED DESCRIPTION OF THE INVENTION

Figure 1:
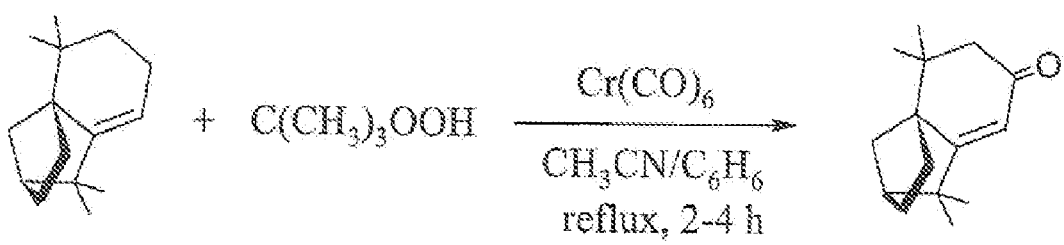
FIG. 1 shows preparation of isolongifolenone 1 from isolongifolene.

We have successfully converted isolongifolene into isolongifolenone 1 (FIG. 1) utilizing tert-butyl hydroperoxide as the oxidant and chromium hexacarbonyl as the catalyst (which can be recycled). This method uses a short reaction time and results in a high purity, high yield product. For example, the conversion rate was about 99% and about 90% isolongifolenone was formed after about 2 h oxidation; at about 3.5 h, the isolongifolene was oxidized to about 100% and about 93% isolongifolenone was achieved. Chemical purity of crude product was about 94%. After flash chromatography purification, chemical purity can be >99%.

Generally, isolongifolenone is produced by reacting a solution containing (−)-isolongifolene, chromium hexacarbonyl, and t-butyl hydroperoxide; the solution generally also contains acetonitrile and benzene. Generally, the solution contains about 1 (e.g., 1) molar isolongifolenone, about 0.3-about 1 (e.g., 0.3-1) molar equivalents of chromium hexacarbonyl, about 2-about 5 (e.g., 2-5) molar equivalents of t-butyl hydroperoxide, and about 80-about 95% (e.g., 80-95%) (w/w) acetonitrile, and about 8-about 9.5% (e.g., 8-9.5%) (w/w) benzene based on isolongifolenone. The solution is heated (generally about 80° to about 82° C. (e.g., 80°-82° C.)) for about 2 to about 4 hours (e.g., 2-4 hours). The solution is then cooled to room temperature (e.g., using an ice-bath), filtered, and the precipitate (chromium hexacarbonyl) is washed with cold benzene. The filtrate is diluted with hexane and washed with water, brine, and dried over $Na_2SO_4$. The solvent is evaporated under reduced pressure to give crude product (about 94% (e.g., 94%) purity). The isolongifolenone may be purified (e.g., by a flash chromatography on silica gel 60 Å (Fisher, 230-400 mesh) using hexane-ethyl acetate as eluent) to provide isolongifolenone 1 as a white semi-solid at room temperature (>about 99% (e.g., >99%) purity).

To recycle the catalyst, the liquid phase is withdrawn by glass pipette from the reaction flask when the reaction is finished and the precipitate is washed several times with cold benzene; and then 15% less amount of isolongifolene (liquid phase may dissolve a little catalyst) and oxidant can be used for subsequent oxidation.

Isolongifolenone is known to have importance in industry because its derivatives are widely used in fragrances, perfumes, space sprays, cosmetics, detergents, deodorants, fabrics, fibers, and paper products (GB Patent No. 1,256,535; U.S. Pat. No. 3,647,847; GB Patent No. 1505821; U.S. Pat. No. 3,718,698; DE Patent No. 10,038,544 A1; U.S. Pat. No. 6,734,159; DeBruyn, M., et al., Agnew. Chem. Internat. Edit., 42: 5333-5336 (2003)). In addition, isolongifolenone and other derivatives have been discovered to be active against tyrosinase, which is a multifunctional copper-containing enzyme for melanin biosynthesis in plants and animals (Choudhary, M. I., et al., Helv. Chim. Ada, 86: 3450-3460 (2003)). Recently, crude extracts from the stems and leaves of *Humiria balsamifera* St. (Aubl.) Hill (Humiriaceae), which is distributed commonly in the Amazon and northeast regions of Brazil, have been found to possess antimalarial activity (Da Silva, T. B. C., et al., Pharm. Biol., 42: 94-97 (2004)). Several compounds, including isolongifolenone, have been isolated and identified as the natural products in these plant species.

We have also found that isolongifolenone can be used to repel arthropods. Thus the present invention also relates to a method for repelling arthropods involving treating an object or area with an arthropod repelling effective amount of isolongifolenone (and optionally a carrier or carrier material known in the art). The method of the present invention may utilize a composition containing isolongifolenone and optionally a carrier or carrier material.

An insect repellent is any compound or composition which deters insects from biting and feeding on a host. Thus the term "repelling" is defined as inhibiting feeding by arthropods when a chemical is present in a place where insects (e.g., *Aedes aegypti*) would, in the absence of the chemical, feed, and it also includes causing arthropods (e.g., flies and ticks) to make oriented movements away from a source of chemical repellent (Dethier, V. L., et al., J. Econ. Ent., 53: 134-136 (1960)). Thus, the term "repelling" also includes reducing the number of arthropod (e.g., *Aedes aegypti*) bites on a treated area or object (e.g., mammalian skin which has been treated topically with the compositions or compounds of the present invention) when compared to the same area or object which is untreated, and the term "repelling" also includes causing arthropods (e.g., ticks) to make oriented movements away from a treated area or object (e.g., mammalian skin which has been treated topically with the compositions or compounds of the present invention) when compared to the same area or object which is untreated.

The method for repelling arthropods from an object (e.g., mammals such as humans) or area (e.g., a surface such as human skin) involves treating (or exposing) the object or area with isolongifolenone (optionally including a carrier material or carrier). The terms "object" or "area" as used herein include any place where the presence of target pests is not desirable, including any type of premises, which can be out-of-doors, such as in gardens, lawns, tents, camping bed nets, camping areas, and so forth, or indoors, such as in barns, garages, commercial buildings, homes, and so forth, or any area where pests are a problem, such as in shipping or storage containers (e.g., bags, boxes, crates, etc.), packing materials, bedding, and so forth; also includes the outer covering of a living being, such as skin, fur, hair, or clothing.

Isolongifolenone and compositions containing isolongifolenone can therefore be used for repelling harmful or troublesome arthropods such as blood-sucking/feeding and biting insects, ticks and mites.

The arthropods include mosquitoes (for example *Aedes, Culex* and *Anopheles* species), sand flies (for example *Phlebotomus* and *Lutzomyia* species), bed buds (for example *Cimex lectularius*), owl gnats (*Phlebotoma*), blackfly (*Culicoides* species), buffalo gnats (*Simulium* species), biting flies (for example *Stomoxys calcitrans*), tsetse flies (*Glossina* species), horseflies (*Tabanus, Haematopota* and *Chrysops* species), house flies (for example *Musca domestica* and *Fannia canicularis*), meat flies (for example *Sarcophaga carnaria*), flies which cause myiasis (for example *Lucilia cuprina, Chrysomyia chloropyga, Hypoderma bovis, Hypoderma lineatum, Dermatobia hominis, Oestrus ovis, Gasterophilus intestinalis* and *Cochliomyia hominovorax*), bugs (for example *Cimex lectularius, Rhodnius prolixus* and *Triatoma infestans*), lice (for example *Pediculus humanus, Haematopinus suis* and *Damalina ovis*), louse flies (for example *Melaphagus orinus*), and fleas (for example *Pulex irritans, Cthenocephalides canis* and *Xenopsylla cheopis*) and sand fleas (for example *Dermatophilus penetrans*).

The harmful or troublesome insects include cockroaches (for example *Blattelia germanica, Periplaneta americana, Blatta orientalis* and *Supella supellectilium*), beetles (for example *Sitophilus granarius, Tenebrio molitor, Dermestes lardarius, Stegobium paniceum, Anobium puntactum* and *Hylotrupes bajulus*), termites (for example *Reticulitermes lucifugus*) and ants (for example *Lasius niger*).

The blood-feeding ticks include, for example, *Ornithodorus moubata, Ixodes ricinus, Ixodes scapularis, Boophtlus microplus, Amblyomma americanum,* and *Amblyomma hebreum.,* and mites include, for example, *Sarcoptes scabiei* and *Dermanyssus gallinae.*

The compound according to the invention, which can be used in undiluted or diluted form, can be converted into formulations customary for repellents. It can be used in all the presentation forms customary in cosmetics, for example in the form of solutions, emulsions, gels, ointments, pastes, creams, powders, sticks, sprays or aerosols from spray cans.

For use in the non-cosmetic sector, the compound can be incorporated, for example, into granules, oily spraying agents or slow release formulations.

The formulations are prepared in a known manner by mixing or diluting the compound according to the invention with solvents (for example xylene, chlorobenzenes, paraffins, methanol, ethanol, isopropanol or water), carriers (for example kaolins, aluminas, talc, chalk, highly disperse silicic acid and silicates), emulsifying agents (for example polyoxyethylene fatty acid esters, polyoxyethylene fatty alcohol ethers, alkylsulphonates and arylsulphonates) and dispersing agents (for example lignin, sulphite waste liquors and methylcellulose).

The compound according to the invention can be used as mixtures with other known active compounds (for example sunscreen agents). The formulations in general contain between about 0.1 and about 95% (e.g., 0.1-95%) by weight of active compound, preferably between about 0.5 and about 90% (e.g., 0.5-90%), more preferably between about 0.5 and about 40% (e.g., 0.5-40%).

For protection from arthropods such as blood-sucking insects or ticks or mites, the compound according to the invention is generally either applied to human or animal skin, or items of clothing and other objects are treated with the compound.

The compound according to the invention is also suitable as an additive to impregnating agents for, for example, textile webs, articles of clothing and packaging materials, and as an additive to polishing, cleaning and window-cleaning agents.

The composition of the present invention contains a carrier and the compound. The repellent of the present invention is generally applied with a carrier component. The carrier component can be a liquid or a solid material. As is known in the art, the vehicle or carrier to be used refers to a substrate such as a gel, polymers, or the like. All of these substrates have been used to release insect repellents and are well known in the art.

The amount of the compound used will be at least an effective amount. The term "effective amount," as used herein, means the minimum amount of the compound needed to reduce the number of arthropod (e.g., *Aedes aegypti*) bites on a treated area or object (e.g., mammalian skin which has been treated topically with the compound of the present invention) when compared to the same area or object which is untreated. The term "effective amount," as used herein, also means the minimum amount of the compound needed to cause arthropods to make oriented movements away from a treated area or object (e.g., mammalian skin which has been treated topically with the compound of the present invention) when compared to the same area or object which is untreated. For example, generally about 10-300 (e.g., 10-300) nmole isolongifolenone/$cm^2$ cloth or skin is used, preferably about 10-200 (e.g., 10-200) nmole/$cm^2$ cloth or skin, more preferably about 20-100 (e.g., 20-100) nmole/$cm^2$ cloth or skin, and most preferably about 20-80 (e.g., 20-80) nmole/$cm^2$ cloth or skin. Effective concentrations of the compound in the compositions may vary between about 0.1 and about 95% (e.g., 0.1-95%) by weight, preferably between about 0.5 and about 90% (e.g., 0.5-90%). Of course, the precise amount needed will vary in accordance with the particular repellent composition used; the type of area or object to be treated; the number of hours or days of repelling needed; and the environment in which the area or object is located. The precise amount of repellent can easily be determined by one skilled in the art given the teaching of this application. For example, one skilled in the art could follow the procedure utilized below.

The compound may be used with other repellents or arthropod control agents (e.g., insecticides, chemosterilants or the like). When used, these agents should be used in an amount which, as readily determined by one skilled in the arts, will not interfere with the effectiveness of the compound.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Synthesis of isolongifolenone: Successful conversion of isolongifolenone into isolongifolenone 1 depends on the selectivity of the allylic oxidation of alkene into an $\alpha,\beta$-unsaturated ketone without double bond migration or epoxidation. Our investigations involved the utilization of peroxides, such as hydrogen peroxide, tert-butyl hydroperoxide, and cumene hydroperoxide as the oxidants, with or without chromium hexacarbonyl as the catalyst. The same amount of isolongifolene was used as the starting material in the different reactions and the results are summarized in Table 1.

Without being bound by theory, apparently the production of isolongifolenone 1 was influenced by the oxidants and the catalyst used during certain oxidation processes. It was found that peracetic acid could efficiently oxidize isolongifolene in less than 2 h, but the saturated ketone 4 was the main product whereas the isolongifolenone 1 was less than 1% (entries 4 and 5), and the reaction was not influenced by the catalyst. In the case of cumene hydroperoxide (entries 19-25) isolongifolenone 1 was the predominate product, however 11-24% of other isomers were formed. Hydrogen peroxide gave poor oxidation results, varying amounts of 1 to 5 and other identified compounds being produced (entries 1-3). During the course of these studies it was surprisingly observed that a high degree of allylic oxidation selectivity in the conversion of isolongifolene into isolongifolenone 1 was achieved using tert-butyl hydroperoxide as the oxidant and chromium hexacarbonyl as the catalyst with a surprisingly short reaction time (entries 11-18). For example, the conversion rate surprisingly was about 99% and 90% isolongifolenone 1 was formed after 2 h oxidation. At 3.5 h, the isolongifolene surprisingly was oxidized 100% and 93% isolongifolenone 1 was achieved. However, the conversion rate was only about 38% and less than 80% isolongifolenone 1 was detected in the oxidation products within the chromium hexacarbonyl catalyst after 4 h oxidation (entry 7), indicating that the selectivity of allylic oxidation of isolongifolene was effectively influenced by this catalyst.

General synthesis of isolongifolenone: To a solution of (−)-isolongifolene (300 mg, 1.47 mmol, purity 98% GC, b.p. 255-256° C., Sigma, St. Louis, Mo.) and chromium hexacarbonyl (161 mg, 0.73 mmol) in 4 mL of acetonitrile and 0.4 mL of benzene (benzene promoted the dissolution of isolongifolene into acetonitrile) was added dropwise t-butyl hydroperoxide (0.61 mL, 4.40 mmol). The resulting reaction mixture was boiled gently under reflux at ~82° C. for 4 hours and the reaction was tracked by GC. After the GC peak of starting material, isolongifolene, completely disappeared the reaction mixture was cooled to room temperature using an ice-bath, filtered through a sintered funnel, and the precipitate (chromium hexacarbonyl) was washed with cold benzene (3×4 mL). The filtrate was diluted with hexane and washed with water (3×5 mL), brine, and dried over $Na_2SO_4$. The solvent was evaporated under reduced pressure to give 315.6 mg of crude product (yield 98.4%, purity 93.9%). The isolongifolenone was purified by a flash chromatography on silica gel (g) using hexane-ethyl acetate (5:1 v/v) as eluent to provide 264 mg (1.21 mmol, 82.4% yield, 99.7% purity) of isolongifolenone 1 as a colorless liquid at room temperature.

mp: 31-32° C. $[\alpha]_D^{26}$ −153.30 (c 10.45, MeOH). $^1$H-NMR (CDCl$_3$, 400 MHz): δ 0.94 (3H, s, CH$_3$), 1.00 (3H, s, CH$_3$), 1.03 (3H, s, CH$_3$), 1.08 (3H, s, CH$_3$), 1.96-1.28 (1H, m), 1.35 (1H, d, J=10.2 Hz), 1.57 (1H, m), 1.62 (1H, dq, J=10.2, 2.0 Hz), 1.67-1.73 (1H, m), 1.87 (1H, dd, J=12.0, 4.0 Hz), 1.92 (1H, d, J=4.0 Hz), 2.00 (1H, d, J=16.0 Hz, O=CC—H), 2.33 (1H, d, J=16.0 Hz, O=CC—H), 5.65 (1H, s, =C—H). $^{13}$C-NMR (CDCl$_3$, 100 Hz): δ 24.26, 24.50, 25.32, 25.69, 26.91, 27.76, 34.36, 36.62, 44.00, 46.43, 49.83, 58.54, 116.78, 183.82, 200.10. EI-MS m/z (%): 218 [M]$^+$ (56), 203 (13), 189 (8), 175 (100), 162 (73), 147 (58), 133 (23), 119 (25), 105 (21), 91 (29), 77 (12), 69 (9), 55 (8).

Mosquito Bioassay: Yellowfever mosquito, *Aedes aegypti* (red eye Liverpool strain) and malarial vector mosquito, *Anopheles stephensi* used in the study were from colonies maintained at the Walter Reed Army Institute of Research, Department of Entomology, Silver Spring, Md. The mosquitoes were reared using the procedure of Gerberg et al. (Gerberg, E. J., et al., Manual for mosquito rearing and experimental techniques, 1994, AMCA Inc., Lake Charles, La.). Larvae were fed ground tropical fish flakes (Tetramin Tropical Fish Flakes, Tetra Sales, Blacksburg, Va., www-.tetra-fish.com). Colonies were maintained in a photoperiod of 12:12 h (L:D with lights on at 0600 h) at 27° C. and 80% RH. Adult mosquitoes were supplied with cotton pads moistened with 10% aqueous sucrose solution.

The comparative mosquito biting-deterrent activity of isolongifolenone and N,N-diethyl-3-methylbenzamide (Deet) was evaluated using the mosquitoes *A. aegypti* and *An. stephensi*. Isolongifolenone was synthesized as described earlier. The well known and widely used synthetic repellent chemical Deet (McCabe, E. T., et al., J. Org. Chem., 19: 493-498 (1954)) was purchased from Morflex, Inc., Greensboro, N.C. Deet is often considered to be the best mosquito repellent ever developed (Elston, D. M., J. Am. Acad. Dermatol., 36: 644-645 (1998)) and is used as a golden standard to which new candidate repellents are compared. A comparative bioassay of the two compounds was conducted by using the in vitro K&D module bioassay system (Klun et al. 2005). The K&D in vitro assay system consists of three components: (1) a Plexiglas™ 29.7 cm×7.1 cm K&D module composed of six adjacent cells each designed to hold mosquitoes and each having a rectangular 3×4 cm floor hole that opened and closed by a sliding door; (2) a Plexiglas™ six-well 29.7 cm×7.1 cm water water-bath warmed (38° C.) reservoir with six 3×4 cm wells designed to match the sliding-door openings of the K&D module base and to contain 6 mL warmed human red blood cell wells covered with a collagen membrane (the blood cell-membrane unit simulated a human host for mosquito feeding); and (3) a 29.7×7.1 cm×0.4 cm Teflon® separator having six rectangular openings like the K&D module. In the study, test compounds in 95% ethanol solution were applied to 3×4 cm cloth areas marked with ink pen on a 29.7-cm×7.1-cm strip of organdy cloth. We routinely applied ethanol solutions (115 µL) 0.5 cm outside of the 3×4 mark cloth areas to ensure that mosquitoes were never exposed to any area of untreated cloth. The treated areas (25 nmol/cm$^2$ cloth) matched and covered the collagen membrane covered blood-cell wells of the blood cells reservoir; the 25 nmol compound/cm2 dose was used because previous dose×response bioassays with Deet and other standard repellent compounds showed that at this dose, applied to human skin or cloth, caused ca. 80% suppression of mosquito biting compared to controls (Klun et al. 2005; Klun, J. A., et al., J. Med. Entomology, 40: 293-299 (2003)). The Teflon® separator was placed over the treated cloth. The function of the separator was to prevent direct contact to the K&D module with chemically treated cloth. A bioassay replicate consisted of three treatments: isolongifolenone, Deet, and 95% ethanol treated cloth as control. We used two replicates with treatments randomly positioned over the six-cells of a reservoir. The 25 nmol/cm$^2$ cloth dose was used because it was known from previous bioassays with Deet and other bioactive compounds that the dose suppressed mosquito biting by about 80% compared to controls in replicated assays (Klun et al. 2005, Klun et al. 2003).

The mosquito bioassays were conducted with the in vitro K&D module systems positioned in a Purair ductless chemical fume hood (Air Science USA LLC, Fort Myers, Fla.) from 1300-1600 h over days at 24°-26° C. and 24-51% RH in ambient laboratory light. Mated nulliparous *Ae. aegypti* and *An. stephensi* (5-15 d old) were tested, and they had no water 24 h before testing. Mosquitoes were loaded into each of six adjacent K&D module cells and promptly after loading they were exposed to 2 replicates of the three treatments on the organdy cloth. Routinely, a six-celled K&D module containing five mosquitoes/cell was positioned on the Teflon® separator over cloth air-dried cloth treatments covering the blood-membrane wells, and trap doors of the K&D modules were opened to expose the treatments to the sets of mosquitoes. After a 3-minute exposure, the number of mosquitoes biting through cloth treatments in each cell was recorded and mosquitoes were prodded back into the cells.

In replicated tests, each of the chemical treatments was tested against 200 *A. aegypti* and 200 *An. stephensi* females (40 replicates). The not biting data were converted to proportion then transformed by the standard variance stabilizing transformation for proportions (arcsin, $\sqrt{p}$, where p is the original proportion) in order to fit the assumption of homogeneity of variances for analysis of variance (ANOVA). Not biting means were compared by one-way ANOVA followed by Ryan-Einot-Gabriel-Welsch range test (SPSS 10.0 for Windows for significance at α=0.05 level, George, D., and P. Mallery, SPSS for Windows step by step: A simple guide and reference, 4th ed., 2002, Allyn & Bacon, Boston).

Tick Bioassay: Blacklegged tick (*Ixodes scapularis*) nymphs were reared from larvae obtained from the laboratory colony at Oklahoma State University, Stillwater, Okla., and fed on rats (Beltsville Area Animal Care and Use Committee Protocol #05-0122) at the U.S. Department of Agriculture (USDA), Agricultural Research Service (ARS), Beltsville Agricultural Research Center, Beltsville, Md. Lone star tick (*Amblyomma americanum*) nymphs were obtained from a colony at the USDA, ARS, Knipling-Bushland U.S. Livestock Insects Research Laboratory, Kerrville, Tex. Both species of ticks were maintained at 24° C., ~97% r.h. and LD 16:8 h until testing.

The fingertip bioassay used by Schreck et al. (Schreck, C. E.; Fish, D.; McGovern, T. P. *J. Am. Mosq. Control Assoc.* 1995, 11, 136-140) was modified (Carroll, J. F., et al., Exp. Appl. Acarol., 41: 215-224 (2007); Carroll, J. F., et al., Med. Vet. Entomol., 19:101-106 (2005)) by applying treatments to the outer layer of a strip of cloth (organdy) later doubly wrapped around the middle phalanx of an index finger. A 7×7 mesh/mm strip of organdy cloth (G Street Fabrics, Rockville, Md.) was cut in the shape of a hockey stick (9 cm long section, 4.5 cm short section, 4-4.5 cm wide) so that when the cloth was wrapped twice around the middle phalanx of the index finger it completely covered the area between the deepest creases of the distal and middle joints of the finger of JFC. The cloth extended 5-6 mm proximally beyond the deepest crease of the middles joint and overlapped 1-3 mm. With the strip of cloth in place, the boundaries of the area to receive the repellent treatment area (between the deepest creases of the distal and middle joints) were marked on the cloth with a lead pencil. This cloth was used a template for tracing the boundaries on other cloths.

Stoichiometrically equivalent stock 95% ethanol solutions of the compounds were prepared: 50 nmol Deet/µL and 50 nmol isolongifolenone/µL for use in all bioassays. The volumes of the respective solutions and used to generate 155 nmole repellent doses/$cm^2$ cloth were based on the dimensions of the middle phalanx of the left index finger of JFC. The volume of the treated solutions required to give the desired nmoles/$cm^2$ cloth dosages was calculated from the average of the circumferences of the two finger joints multiplied by the distance between the deepest crease of each joint.

A repellent solution (52 µL) or ethanol (control) of the same volume was applied to the designated treatment area on the cloth and allowed to dry. As with Schreck et al. (1995), it was necessary to screen *I. scapularis* nymphs for active individuals. While the treated cloth dried, *I. scapularis* nymphs were transferred by forceps from a holding vial to a finger. Ten ticks that crawled $\geq$ 5 mm were sequestered in a Petri dish that had been glued inside a larger Petri dish and water added to the space between their sides to form a moat. After the cloth dried (10-12 min), it was wrapped twice around the index finger. To keep the cloth wrapped around the finger, three small dabs of beeswax were smeared on the upper surface of the inner layer of cloth at the edge of the overlap and pressure applied for 10 s. Using forceps, the 10 selected ticks were placed on the tip of the horizontally held finger between the nail and the edge of the cloth. When the tenth tick was placed on the finger, the finger was slowly tipped vertically with the tip downward. The locations of the ticks were recorded at 1, 3, 5, 10 and 15 min after their release on the finger. Host-seeking *Am. americanum* are notably more active than *I. scapularis*, so 10 *A. americanum* nymphs were allowed to crawl directly from an open vial onto the fingertip. For both species, the finger was held over moated Petri dishes while $\geq$ 1 tick was on it. During bioassays temperatures ranged from 23-26° C. and 10-56% R. H. The repellent data were compared by paired samples t-test (SPSS 10.0 for Windows for significance at $\alpha$=0.05 level, George, D., and P. Mallery, SPSS for Windows step by step: A simple guide and reference, 4th ed., 2002, Allyn & Bacon, Boston).

One dose (155 nmole of compound/$cm^2$) of repellent and ethanol were tested against four groups of 10 *Am. americanum* nymphs and four groups of *I. scapularis* nymphs. For dose response test, three doses (19.5, 39, and 78 nmole of compounds/$cm^2$ cloth) of each of Deet, isolongifolenone, and ethanol (95%) were tested against four groups of 10 *I. scapularis* nymphs. Ticks were considered repelled if they had dropped from the finger or were on the untreated tip at 10 min after they were placed on the finger.

Figure 2:
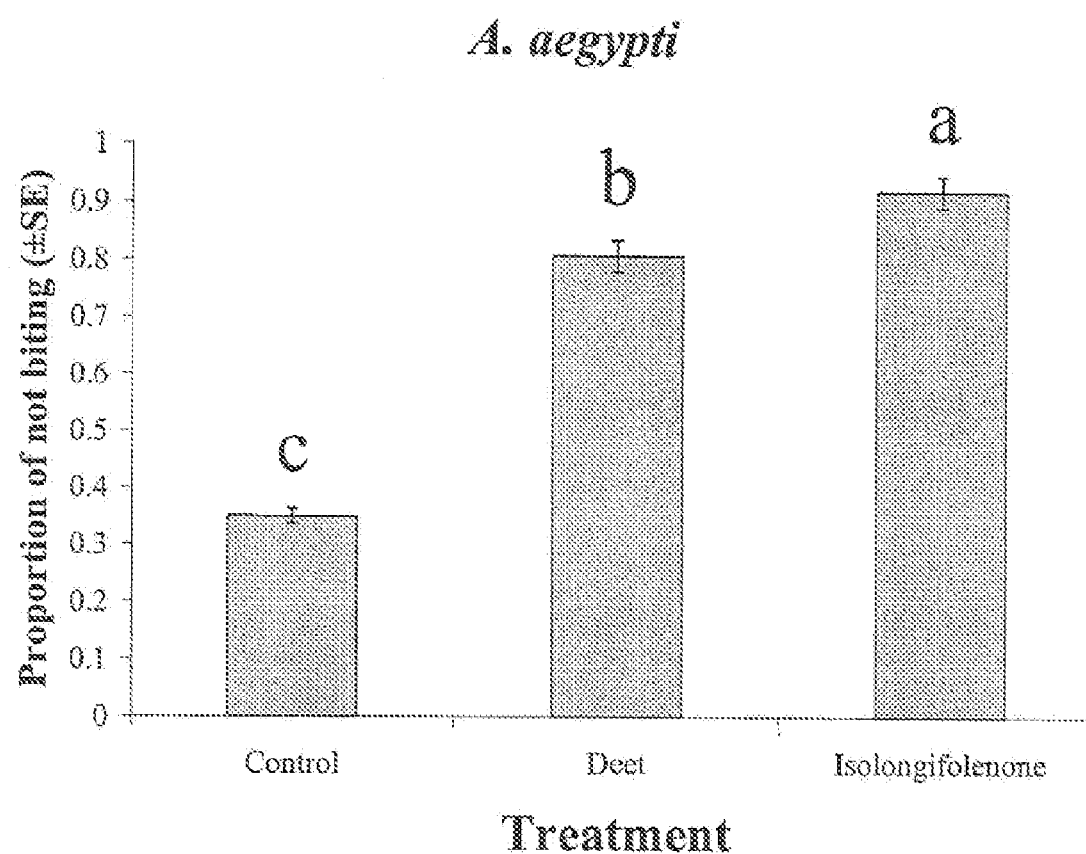
FIG. 2 shows the mean of non-biting proportion of female *Aedes aegypti* (±SE) exposed to isolongifolenone (25 nmole/$cm^2$ cloth) and Deet (25 nmole/$cm^2$ cloth) and a blank control (95% ethanol) in an in vitro K&D module (Klun & Debboun module bioassay system; Klun, J. A., et al., J. Amer. Mosquito Control Assoc., 21: 64-70 (2005)). The total number of female *A. aegypti* tested for each treatment was 200. Means followed by the different letters are significantly different at $\alpha=0.05$ [n=40, F(2,117)=117.76, P<0.001].
Figure 3:
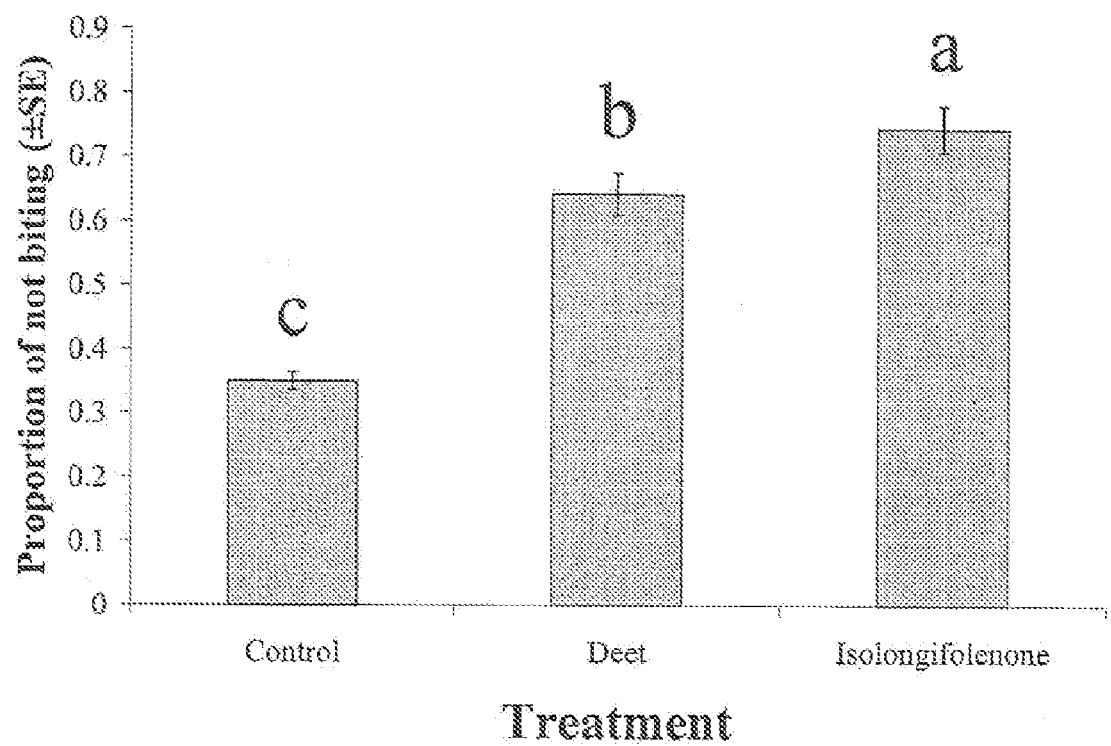
FIG. 3 shows the mean of non-biting proportion of female *Anopheles stephensi* (±SE) exposed to isolongifolenone (25 nmole/$cm^2$ cloth) and Deet (25 nmole/$cm^2$ cloth) and a blank control (95% ethanol) in an in vitro K&D module. The total number of female *An. stephensi* tested for each treatment was 200. Means followed by the different letters are significantly different at $\alpha=0.05$ [n=40, F(2,117)=38.85, P<0.001].

Results and Discussion: FIGS. 2 and 3 show the repellency of 25 nmol/$cm^2$ cloth doses of isolongifolenone, Deet, and the control in bioassays with the mosquitoes *A. aegypti* and *An. Stephensi*, respectively. The proportions of mosquitoes that did not bite were significantly greater for isolongifolenone and Deet than for the control (ethanol-treated cloth), and isolongifolenone surprisingly deterred the biting of *A. aegypti* and *An. stephensi* more effectively than Deet.

Figure 4:
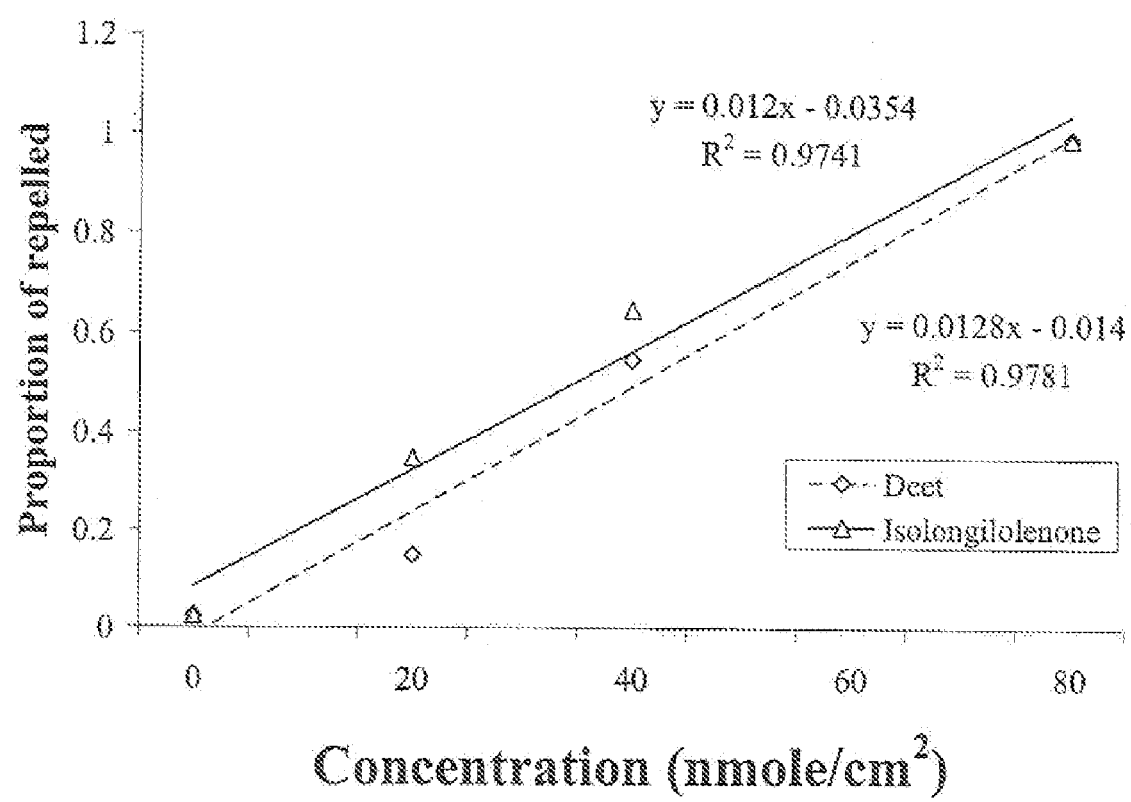
FIG. 4 shows the dose responses of *Ixodes scapularis* nymphs in fingertip bioassays (treated-cloth strip wrapped around finger) to three concentrations of Deet and isolongifolenone (19.5, 39, and 78 nmole of compounds/$cm^2$ cloth) and ethanol (95%) as a blank control (compound concentration of zero). The total number of *I. scapularis* nymphs tested for each treatment was 40.

Table 2 show the results of tick bioassays using 155 nmol/$cm^2$ cloth dose of isolongifolenone and compared to control against the blacklegged tick *I. scapularis* and lone star tick *Am. americanum*. Surprisingly, the proportion of ticks repelled by isolongifolenone was significantly higher than for the control (ethanol-treated cloth). Thus isolongifolenone is a new lead compound that represents an alternative to traditional synthetic compounds that have been developed and used for protection against blood-feeding arthropods that vector human disease. Our experimental data indicated that the increasing proportion of *I. scapularis* nymphs repelled by isolongifolenone and Deet over increasing concentrations (19.5, 39, and 78 nmole of compounds/$cm^2$ cloth) followed first order kinetics. Dose response curves were best described by equations: Y=0.012x–0.0354, $r^2$=0.9741 for isolongifolenone and Y=0.0128x–0.014, $r^2$=0.9781 for Deet, respectively (FIG. 4). At 78 nmole/$cm^2$ cloth, both isolongifolenone and Deet repelled 100% of the *I. scapularis* nymphs (FIG. 4). However, at 39 nmole/$cm^2$ cloth, isolongifolenone and Deet repelled 65% and 55% of the *I. scapularis* nymphs respectively and at 19.5 nmole/$cm^2$ cloth isolongifolenone and Deet repelled 35% and 15% respectively.

Our data thus showed the repellent effects of isolongifolenone against blood-feeding arthropods. Bioassays showed that isolongifolenone deterred the biting of two species of mosquitoes, yellowfever mosquito, *Aedes aegypti* and malarial vector mosquito, *Anopheles stephensi*, more effectively than Deet, a benchmark repellent used worldwide. We also found that the compound repelled the blacklegged tick, *Ixodes scapularis*, as effectively as Deet. However, at lower concentration the isolongifolenone showed higher effectiveness against *I. scapularis* compared to Deet.

All of the references cited herein, including U.S. Patents, are incorporated by reference in their entirety. Also incorporated by reference in their entirety are the following references: Muthyala, R. S., et al., J. Med. Chem., 46: 1589-1602 (2003); Novak, R. J., and E. J. Gerberg, J. Am. Mosquito Control Assoc. (Supplement), 21: 7-11 (2005); Shiino, M., et al., Med. Chem., 9: 1233-1240 (2001).

Thus, in view of the above, the present invention concerns (in part) the following:

A method for making isolongifolenone, comprising (or consisting essentially of or consisting of) reacting (−)-isolongifolene with chromium hexacarbonyl and t-butyl hydroperoxide to make isolongifolenone.

The above method, wherein said method comprises (or consists essentially of or consists of) reacting (−)-isolongifolene with chromium hexacarbonyl and t-butyl hydroperoxide in a solution containing acetonitrile and benzene.

The above method, wherein said solution contains about 1 molar isolongifolenone, about 0.3-about 1 molar equivalents of chromium hexacarbonyl, and about 2-about 5 molar equivalents of t-butyl hydroperoxide, and about 80-about 95% (w/w) acetonitrile and about 8-about 9.5% (w/w) benzene based on isolongifolenone.

The above method, wherein said reacting is at a temperature of about 80° to about 82° C.

The above method, wherein said reacting is for about 2 to about 4 hours.

The above method, wherein the conversion rate was about 99% and about 90% isolongifolenone was formed after a reaction time of about 2 hours.

The above method, wherein the conversion rate was about 100% and about 93% isolongifolenone was formed after a reaction time of about 3.5 hours.

The above method, wherein the purity of the isolongifolenone is about 94%.

The above method, further comprising purifying said isolongifolenone to more than about 99% purity.

A method for repelling arthropods, method comprising (or consisting essentially of or consisting of) treating an object or area with an arthropod repelling effective amount of isolongifolenone and optionally a carrier or carrier material.

The above method, wherein said arthropod repelling effective amount of isolongifolenone is about 10-about 300 nmole isolongifolenone/cm$^2$ or is about 10-about 200 nmole isolongifolenone/cm$^2$ or is about 20-about 100 nmole isolongifolenone/cm$^2$ or is about 20-about 80 nmole isolongifolenone/cm$^2$.

The above method, wherein said arthropods are selected from the group consisting of *Aedes* species, *Culex* species, *Anopheles* species, *Ornithodorus* species, *Ixodes* species, *Boophilus* species, *Amblyomma* species, and mixtures thereof.

The above method, wherein said arthropods are selected from the group consisting of *Aedes aegypti, Anopheles stephensi, Ixodes scapularis, Amblyomma americanum*, and mixtures thereof.

The above method, wherein said arthropods are selected from the group consisting of *Aedes aegypti, Anopheles stephensi*, and mixtures thereof.

The above method, wherein said arthropods are selected from the group consisting of *Ixodes scapularis, Amblyomma americanum*, and mixtures thereof.

A method for repelling arthropods, method comprising (or consisting essentially of or consisting of) treating an object or area with an arthropod repelling effective amount of isolongifolenone and a carrier or carrier material.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Oxidation of isolongifolene under different conditions[a]

| Entry | Oxidants | Catalyst | Time (h) | Conversion (%) | Product ratios (%)[b,c] | | | | | |
|---|---|---|---|---|---|---|---|---|---|---|
| | | | | | (2) | (3) | (4) | (5) | (1) | Others[d] |
| 1 | H$_2$O$_2$ | Cr(CO)$_6$ | 1.0 | 18.7 | 23.5 | 11.5 | 16.4 | 7.7 | 35.3 | 5.6 |
| 2 | H$_2$O$_2$ | Cr(CO)$_6$ | 2.5 | 19.1 | 22.9 | 11.1 | 16.2 | 7.6 | 36.4 | 5.8 |
| 3 | H$_2$O$_2$ | Cr(CO)$_6$ | 18.0 | 46.6 | 14.4 | 6.2 | 23.4 | 7.4 | 37.7 | 10.9 |
| 4 | CH$_3$COOOH | — | 1.8 | 99.8 | 0 | 0 | 83.9 | 3.1 | 0.8 | 12.2 |
| 5 | CH$_3$COOOH | Cr(CO)$_6$ | 1.5 | 100 | 0 | 0 | 80.2 | 4.6 | 0.5 | 14.7 |
| 6 | (CH$_3$)$_3$COOH | — | 1.0 | 17.9 | 2.5 | 2.4 | 7.3 | 7.8 | 75.4 | 4.6 |
| 7 | (CH$_3$)$_3$COOH | — | 4.0 | 37.5 | 1.7 | 1.3 | 6.4 | 6.1 | 79.8 | 4.7 |
| 8 | (CH$_3$)$_3$COOH | — | 16.0 | 70.8 | 0.9 | 0.8 | 2.9 | 4.0 | 84.7 | 6.7 |
| 9 | (CH$_3$)$_3$COOH | — | 21.0 | 84.8 | 0.7 | 0.6 | 3.2 | 4.0 | 84.7 | 6.8 |
| 10 | (CH$_3$)$_3$COOH | — | 23.5 | 95.1 | 0.1 | 0.1 | 2.4 | 3.0 | 77.1 | 17.3 |
| 11 | (CH$_3$)$_3$COOH | Cr(CO)$_6$ | 0.5 | 35.2 | 1.1 | 0.9 | 1.1 | 5.1 | 66.2 | 25.6 |
| 12 | (CH$_3$)$_3$COOH | Cr(CO)$_6$ | 1.0 | 88.7 | 1.5 | 0.7 | 1.1 | 2.7 | 85.0 | 9.0 |
| 13 | (CH$_3$)$_3$COOH | Cr(CO)$_6$ | 1.5 | 97.0 | 1.3 | 0.6 | 1.0 | 2.4 | 88.6 | 6.1 |
| 14 | (CH$_3$)$_3$COOH | Cr(CO)$_6$ | 2.0 | 98.9 | 1.3 | 0.6 | 1.2 | 2.1 | 90.7 | 4.1 |
| 15 | (CH$_3$)$_3$COOH | Cr(CO)$_6$ | 2.5 | 99.5 | 1.4 | 0.7 | 2.2 | 1.2 | 91.5 | 3.0 |
| 16 | (CH$_3$)$_3$COOH | Cr(CO)$_6$ | 3.0 | 99.6 | 1.5 | 0.8 | 1.5 | 1.9 | 91.7 | 2.6 |
| 17 | (CH$_3$)$_3$COOH | Cr(CO)$_6$ | 3.5 | 100 | 1.4 | 0.8 | 2.1 | 1.1 | 93.0 | 1.2 |
| 18 | (CH$_3$)$_3$COOH | Cr(CO)$_6$ | 4.0 | 100 | 1.5 | 1.0 | 2.3 | — | 93.2 | 2.0 |
| 19 | C$_6$H$_5$C(CH$_3$)$_2$OOH | — | 2.0 | 59.2 | — | — | 10.5 | 5.9 | 76.6 | 6.9 |
| 20 | C$_6$H$_5$C(CH$_3$)$_2$OOH | — | 4.5 | 73.4 | 1.0 | 1.1 | 7.8 | 6.3 | 76.6 | 7.2 |
| 21 | C$_6$H$_5$C(CH$_3$)$_2$OOH | — | 70.0 | 76.6 | 1.3 | 1.3 | 4.7 | 6.6 | 81.5 | 4.6 |
| 22 | C$_6$H$_5$C(CH$_3$)$_2$OOH | Cr(CO)$_6$ | 1.0 | 65.3 | — | — | 2.0 | 4.9 | 88.9 | 4.2 |
| 23 | C$_6$H$_5$C(CH$_3$)$_2$OOH | Cr(CO)$_6$ | 4.0 | 80.6 | 1.1 | 0.8 | 1.4 | 4.4 | 88.0 | 4.3 |
| 24 | C$_6$H$_5$C(CH$_3$)$_2$OOH | Cr(CO)$_6$ | 21.0 | 86.3 | 1.3 | 1.0 | 0.6 | 5.6 | 88.3 | 3.2 |
| 25 | C$_6$H$_5$C(CH$_3$)$_2$OOH | Cr(CO)$_6$ | 45.0 | 86.7 | 1.2 | 1.0 | 1.0 | 5.4 | 88.5 | 2.9 |

[a]All chemicals were used in the same ratio.
[b]Determined by GC and GC-MS.
[c]
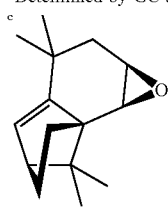

TABLE 1-continued

Oxidation of isolongifolene under different conditions[a]

| Entry | Oxidants | Catalyst | Time (h) | Conversion (%) | Product ratios (%)[b,c] | | | | | Others[d] |
|---|---|---|---|---|---|---|---|---|---|---|
| | | | | | (2) | (3) | (4) | (5) | (1) | |

[structure 3]

[structure 4]

[structure 5]

[d]Consisted of several unidentified components.

TABLE 2

Percent of tick nymphs repelled by isolongifolenone in fingertip bioassays (155 nmol/cm² cloth). Ticks that were on untreated fingertip or had fallen off the finger at 10 min after they were released on the finger were considered repelled.*

| Species | Treatment | Proportion Repellency | t | P |
|---|---|---|---|---|
| I. scapularis | Control | 0.06 | | |
| | Isolongifolenone | 1.0 | −28.0 | <0.001 |
| Am. americanum | Control | 0 | | |
| | Isolongifolenone | 0.725 | −7.03 | 0.006 |

*Three groups of 10 tick nymphs of I. scapularis and four groups of Am. americanum were tested with isolongifolenone and control.

We claim:

1. A method for making isolongifolenone, said method comprising reacting (−)-isolongifolene with chromium hexacarbonyl and t-butyl hydroperoxide to make isolongifolenone.

2. The method according to claim 1, wherein said method comprising reacting (−)-isolongifolene with chromium hexacarbonyl and t-butyl hydroperoxide in a solution containing acetonitrile and benzene.

3. The method according to claim 2, wherein said solution contains about 1 molar isolongifolene, about 0.3-about 1 molar equivalents of chromium hexacarbonyl, and about 2-about 5 molar equivalents of t-butyl hydroperoxide, and about 80-about 95% (w/w) acetonitrile and about 8-about 9.5% (w/w) benzene based on isolongifolene.

4. The method according to claim 1, wherein said reacting is at a temperature of about 80° to about 82° C.

5. The method according to claim 1, wherein said reacting is for about 2 to about 4 hours.

6. The method according to claim 1, wherein the conversion rate was about 99% and about 90% isolongifolenone was formed after a reaction time of about 2 hours.

7. The method according to claim 1, wherein the conversion rate was about 100% and about 93% isolongifolenone was formed after a reaction time of about 3.5 hours.

8. The method according to claim 1, wherein the purity of said isolongifolenone is about 94%.

9. The method according to claim 8, further comprising purifying said isolongifolenone to more than about 99% purity.

10. A method for repelling arthropods, said method comprising treating an object or area with an arthropod repelling effective amount of isolongifolenone and optionally a carrier or carrier material.

11. The method according to claim 10, wherein said arthropod repelling effective amount of isolongifolenone is about 10-about 300 nmole isolongifolenone/cm².

12. The method according to claim 10, wherein said arthropod repelling effective amount of isolongifolenone is about 10-about 200 nmole isolongifolenone/cm².

13. The method according to claim 10, wherein said arthropod repelling effective amount of isolongifolenone is about 20-about 100 nmole isolongifolenone/cm².

14. The method according to claim 10, wherein said arthropod repelling effective amount of isolongifolenone is about 20-about 80 nmole isolongifolenone/cm$^2$.

15. The method according to claim 10, wherein said arthropods are selected from the group consisting of *Aedes* species, *Culex* species, *Anopheles* species, *Ornithodorus* species, *Ixodes* species, *Boophilus* species, *Amblyomma* species, and mixtures thereof.

16. The method according to claim 10, wherein said arthropods are selected from the group consisting of *Aedes aegypti, Anopheles stephensi, Ixodes scapularis, Amblyomma americanum*, and mixtures thereof.

17. The method according to claim 10, wherein said arthropods are selected from the group consisting of *Aedes aegypti, Anopheles stephensi*, and mixtures thereof.

18. The method according to claim 10, wherein said arthropods are selected from the group consisting of *Ixodes scapularis, Amblyomma americanum*, and mixtures thereof.

* * * * *